US005770152A

United States Patent [19]

Schuster et al.

[11] Patent Number: 5,770,152
[45] Date of Patent: Jun. 23, 1998

[54] COLLAPSIBLE CONTAINER FOR MEASURING PARTICLES IN A SAMPLE FLUID

[75] Inventors: Jeffrey A. Schuster; Peter M. Lloyd, both of Oakland; Igor Gonda, San Francisco; David Cipolla, Belmont, all of Calif.

[73] Assignee: Aradigm Corporation, Hayward, Calif.

[21] Appl. No.: 749,610

[22] Filed: Nov. 18, 1996

[51] Int. Cl.[6] ........................................... G01N 7/00
[52] U.S. Cl. .................. 422/73; 422/68.1; 422/82.13; 422/101; 436/10; 436/69; 436/70; 436/148; 436/177; 436/178; 73/61.71; 73/61.72; 73/61.73; 73/863.64; 73/864.62; 73/864.81
[58] Field of Search .................. 422/68.1, 82.13, 422/73, 101; 436/10, 69, 70, 148, 177, 178; 73/61.71, 61.72, 61.73, 863.64, 864.62, 864.81

[56] References Cited

U.S. PATENT DOCUMENTS

| | | | |
|---|---|---|---|
| 3,463,357 | 8/1969 | MacLean, Jr. et al. | 73/864.62 |
| 3,893,334 | 7/1975 | Williams | 73/61.73 |
| 3,900,290 | 8/1975 | Hornstra | 23/230 B |
| 4,461,186 | 7/1984 | Brannstrom et al. | 73/864.62 |
| 4,473,296 | 9/1984 | Shofner et al. | 356/336 |
| 4,635,482 | 1/1987 | Gowing | 73/864.62 |
| 4,765,963 | 8/1988 | Mukogawa et al. | 436/39 |
| 4,786,423 | 11/1988 | Mukogawa et al. | 73/61.73 |
| 5,011,286 | 4/1991 | Petralli | 356/343 |
| 5,076,097 | 12/1991 | Farrin et al. | 73/61.72 |
| 5,095,740 | 3/1992 | Hodgson et al. | 73/61.73 |
| 5,239,861 | 8/1993 | Fujita et al. | 73/61.73 |
| 5,266,495 | 11/1993 | Lapidus | 73/61.73 |
| 5,268,304 | 12/1993 | Inman et al. | 436/172 |
| 5,345,079 | 9/1994 | French et al. | 250/288 |
| 5,376,878 | 12/1994 | Fisher | 324/71.4 |
| 5,385,043 | 1/1995 | Fitch et al. | 73/61.73 |
| 5,497,763 | 3/1996 | Lloyd et al. | 128/200.14 |
| 5,522,385 | 6/1996 | Lloyd et al. | 128/203.26 |
| 5,544,646 | 8/1996 | Lloyd et al. | 128/200.14 |
| 5,660,166 | 8/1997 | Lloyd et al. | 128/200.14 |

OTHER PUBLICATIONS

The United States Pharmacopeia, The National Formulary, 1995. "Particulate Matter in Injections," United States Pharmacopeial Convention, Inc., Rockville, MD, pp. 1813–1819

*Primary Examiner*—Jill Warden
*Assistant Examiner*—Sharidan Carrillo
*Attorney, Agent, or Firm*—Bozicevic and Reed LLP; Karl Bozicevic, Esq.

[57] ABSTRACT

A device and method for the detection of small particles in a fluid. The device is a collapsible sample container having a opening which is covered, at least in part, by a porous membrane having a plurality (e.g., 100) of pores therein having a pore diameter equal to or smaller than the diameter of the particles to be detected (e.g., 01. to 100 microns). A means for collapsing the container to extrude the liquid sample through the membrane pores is provided along with a means for detecting pressure during the extrusion. The size and number of particles in the liquid is calculated by relating the extrusion pressure required to a pre-calibrated standard. When a constant pressure is applied the rate at which fluid is extruded decreases as the pores of the membrane become clogged with particles. The greater number of particles in the sample tested the greater the number of pores which will become clogged with particles which causes an increase in the amount of time or pressure needed to extrude a given volume of the sample through the porous membrane. The number of pores per unit area and pore size can be varied depending on the probable size and concentration of the particles in the liquid be tested.

4 Claims, 9 Drawing Sheets

Extrusion Profiles for a 0.01% Solution of 0.5 Micron Diameter Polystyrene Spheres

Extrusion Profiles for a 0.1% Solution of 0.5 Micron Diameter Polystyrene Spheres

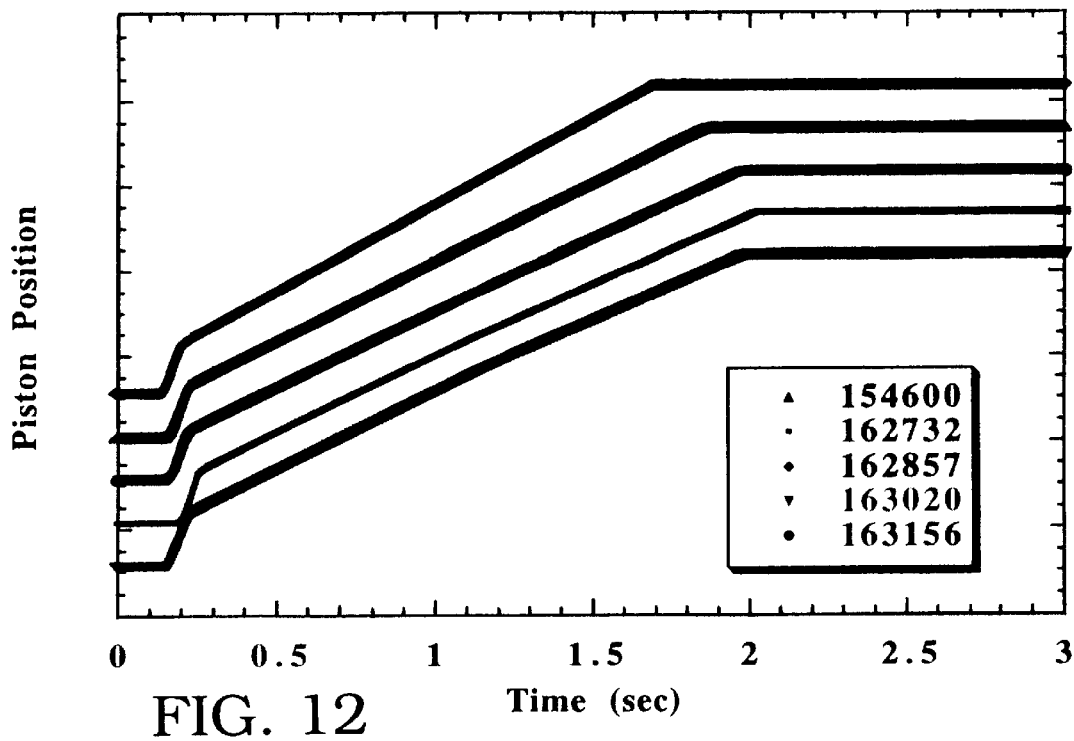
FIG. 12 Extrusion Profiles for a 1.0% Solution of 0.5 Micron Diameter Polystyrene Spheres
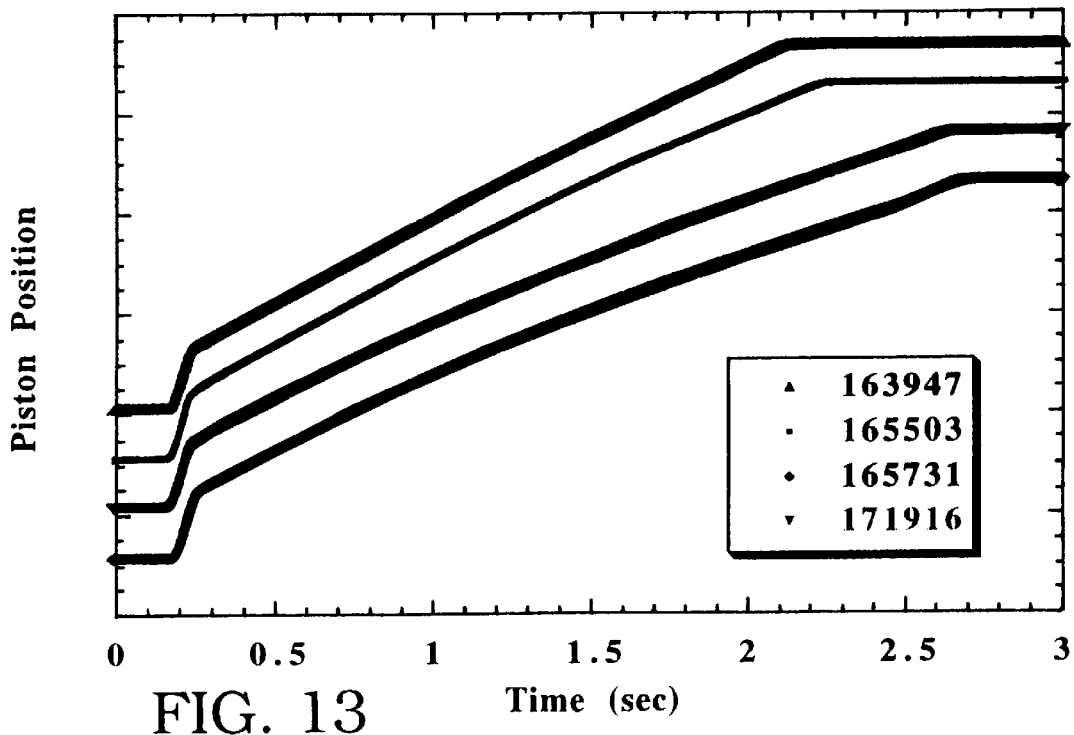
FIG. 13 Extrusion Profiles for a 0.01% Solution of 1.0 Micron Diameter Polystyrene Spheres

Extrusion Profiles for a 0.1% Solution of 1.0 Micron Diameter Polystyrene Spheres

Extrusion Profiles for a 1.0% Solution of 1.0 Micron Diameter Polystyrene Spheres

Extrusion Profiles for AERx Packets filled with ≈ 530 2.0 Micron Diameter Polystyrene Spheres

Extrusion Profiles for AERx Packets filled with ≈ 5300 2.0 Micron Diameter Polystyrene Spheres
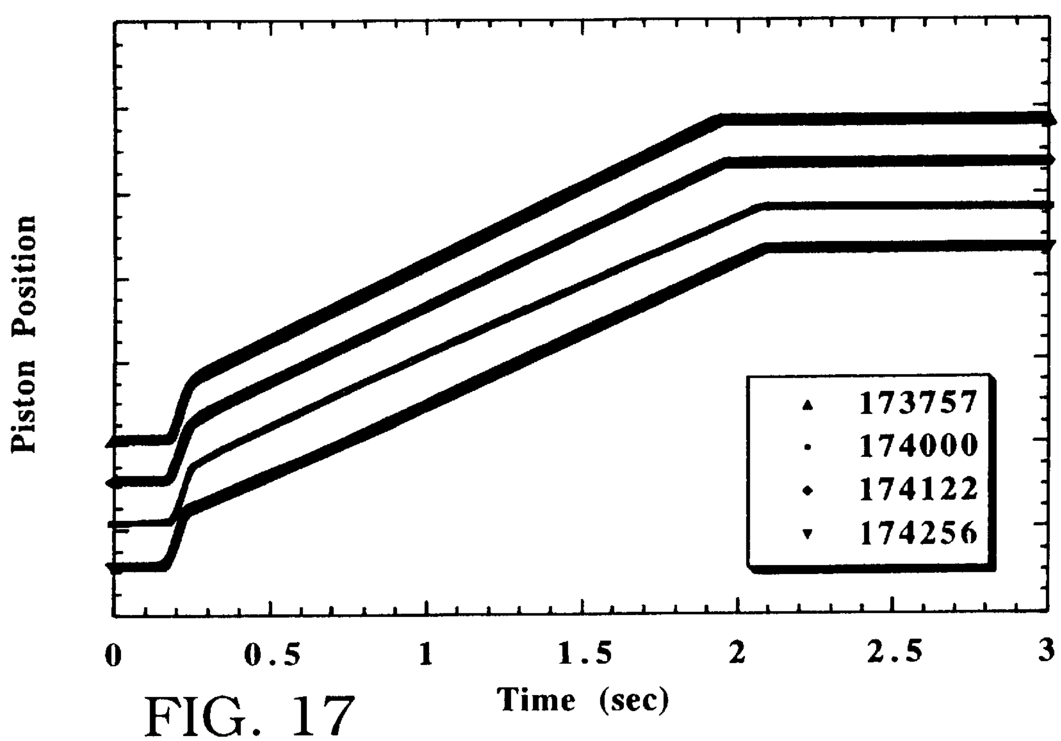
FIG. 17

Extrusion Profiles for AERx Packets filled with ≈ 53000 2.0 Micron Diameter Polystyrene Spheres

COLLAPSIBLE CONTAINER FOR MEASURING PARTICLES IN A SAMPLE FLUID

FIELD OF THE INVENTION

The invention relates generally to devices and methods for detecting small particles in a fluid and particularly to a device and method for determining if a liquid includes particles as well as information about the size and concentration of particles in a liquid.

BACKGROUND OF THE INVENTION

Devices which measure and count particles in a fluid are well known. Such devices are employed, for example, by semiconductor wafer manufacturers to monitor the extent of airborne particulate matter in a clean room. Pharmaceutical manufacturers employ such devices for the detection and control of foreign particles. To a lesser extent of accuracy, smoke detectors also measure particle concentration.

One method of particle detection is the light blockage particle counting, or light obscuration, method. Light obscuration sensors work on the principle of the casting of a shadow onto a photodetector as a flow of particle-laden fluid is directed through a light beam generated by an incandescent lamp. A more sensitive method is the light scattering method. As a particle passes through a light beam, the particle scatters light. For a stationary particle, the amount of scattered light is a function of the particle size, the wavelength and intensity of the incident light, and the difference between the light scattering properties of the particle and the surrounding medium. A laser source may be used to generate the light beam and the scattered light is sensed by a detector which provides readable signals indicative of particle size.

One device and method for particle detection is disclosed in U.S. Pat. No. 5,011,286, issued Apr. 30, 1991 to Petralli which includes a plurality of sample regions. A sensor body has internal walls which define spaced apart sample regions, with each sample region having an inlet port and an exhaust port. An aggregate sample flow is divided into partial flows which are directed from the inlet port to the exhaust port of an associated sample region. A light source, typically a laser, is positioned to project an incident beam along a light path which intersects each of the partial sample flows through the sample regions. Particles contained within the partial sample flows scatter light as the particles pass through the incident beam. The light from a sample region is directed to a photodetector which provides a signal corresponding to the sensed light. Particle detection in each sample region is operationally independent of the others, but the information is combined to provide a total particle count of the aggregate sample flow. Alternatively, the apparatus may be utilized to provide simultaneous particle detection of separate sources of particle-bearing gas. For example, adjacent clean room areas may be monitored channelling separate sample flows directly into separate inlet ports of adjacent sample regions.

Such devices and method generally require (1) and light source, (2) a photodetector, (3) a means for interpreting the photodetector signals and (4) the presence of particle which absorb or deflect light. The present invention endeavors to provide a device and method for the detection of small particles which does not require 1–4 above.

SUMMARY OF THE INVENTION

A device and method for the detection of small particles in a fluid is disclosed. The device is comprised of a sample container which may be collapsible having a opening which is covered, at least in part, by a porous membrane having a plurality (e.g., 100) of pores therein having a pore diameter equal to or smaller than the diameter of the particles to be detected (e.g., a pore diameter in the range of 01. to 100 microns). A means for collapsing the container or applying pressure to its contents to extrude the liquid sample through the membrane pores is provided along with a means for detecting a quantity such as time, force and/or pressure during the extrusion. Alternatively, the amount of pressure applied by a device is set at a given level without the need to measure a parameter. At a very basic level the invention makes it possible to determine whether or not a sample fluid contains any particles i.e., provides a "yes" or "no" answer regarding whether particles are present. At another level the invention determines not only the presence of but information on the size and/or concentration of particles in the liquid relating the quantity measured such as extrusion pressure or time required to a pre-calibrated standard. When a constant pressure is applied the rate at which fluid is extruded decreases as the pores of the membrane becomes clogged with particles. The greater the concentration of particles in the sample tested the greater the number of pores which will become clogged with particles causing an increase in the amount of time, force or pressure needed to extrude a given volume of sample through the porous membrane. The number of pores per unit area, pore size, or porosity can be varied depending on the probable size and concentration of the particles expected to be in the liquid being tested.

An object of the invention is to provide a device and method for determining whether a sample fluid includes small particles.

Another object of the invention is to provide a device and method which can easily, and economically make accurate measurements of the size and concentration of small particles in a liquid.

An advantage of the invention is that it can detect the presence of and/or measure the size and concentration of particles which are invisible to detection or at least not readily detectable via a light source and photodetector.

A feature of the invention is that the number of pores per unit area, pore diameter, and porosity can be varied as needed for any particular situation.

Another object is to provide a series of sample containers which are connected and which have pores of the same size on the membrane of any individual container and which have the same or slightly different pore sizes, porosity, and/or pore density on the membrane of different containers.

Another advantage is that the invention is capable of detecting very small particles at very low concentrations using only a small amount of sample fluid.

Another feature of the invention is that different quantities such as time, pressure and force during extrusion through the membrane are pre-set or are measured and compared to a pre-calibrated standard to determine particle size and concentration.

These and other objects, advantages and features of the present invention will become apparent to those skilled in the art upon reading this disclosure in combination with drawings wherein like numerals refer to like components throughout.

BRIEF DESCRIPTION OF THE DRAWING

FIG. 12 is an extrusion profile for a 1.0% solution of 0.5 micron particles;

FIG. 13 is an extrusion profile for a 0.01% solution of 1.0 micron particles;

FIG. 17 is an extrusion profile for a sample containing approximately 5,300 2.0 micron particles.

DESCRIPTION OF THE PREFERRED EMBODIMENTS

Figure 1:
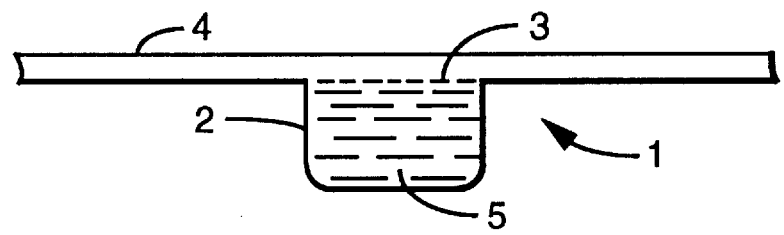
FIG. 1 is a schematic, cross-sectional view of an embodiment of a sample container.

Before the present device and method of detecting particles is described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an assay" includes one or more assays, and reference to "the method of detection" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed herein are provided solely for their disclosure prior to the filing date of the present application. Nothing herein is to be construed as an admission that the invention is not entitled to antedate such publications by virtue of prior invention.

GENERAL OVERVIEW

An embodiment of the invention can operate as follows. First, a liquid sample containing small particles is placed in a collapsible container (see FIGS. 1 and 2) wherein the container includes an opening. Second, the opening of the container is covered, at least in part, by a porous membrane containing a known pore density and pore diameter which diameter is believed to be equal to the mean diameter of the particles in the liquid. Third, an extruding member is forced against the container (see FIG. 3) to extrude the liquid sample through the pores of the membrane. Fourth, a quantity such as the pressure, force and/or time required for extrusion are measured. Fifth, the measured quantity is analyzed and/or compared against pre-calibrated values in order to determine if particles are present in the liquid and/or the concentration of particles of a given size in the liquid.

Any increased pressure, force and/or time needed to extrude is caused by clogging of the pores thereby indicating the presence of particles in the liquid. The greater the concentration of particles of a diameter equal to or greater in diameter than that of the pores the greater the clogging and the greater the increase in force, pressure and/or time needed to extrude the liquid through the membrane. If no difference is observed there may be no particles present. However, the test can be repeated with a membrane having pores with a smaller diameter and/or lower pore density. If the membrane becomes completely clogged the test can be repeated with a membrane with larger pores and/or a higher pore density.

It is important that the concentration of many types of solutions such as pharmaceuticals be precisely known. The concentration can be accurately set when a solution is created by precisely measuring out the amount of solvent and solute. However, the concentration can change over time if the solute begins forming crystals. It is often very difficult to determine the size or concentration of crystalline particles present in a solution. The amount of solute needed to form the crystals may be sufficiently small such that the decrease in concentration due to the crystal formation may not be detectable by conventional means. The present invention is useful not only in detecting if crystals have formed but can be used to detect the size and concentration of crystals formed. Further, such information can be used to determine the decrease in solute concentration caused by the crystal formation.

In addition to determining whether crystals form in a solution and the size and concentration of crystals the present invention can determine presence of or the size and concentration of any particles present in a liquid such as contaminants. Conventional methods may not be able to detect such contaminants for reasons such as (A) the particles are translucent and are being measured by a detector which is only activated when a particle blocks the transmission of light (B) the particles reflect light in a manner which distorts detection; (C) the particles are too small for detection by conventional means; and (D) the particles are present in too small of a concentration for detection by conventional means.

Definition

The terms "porous membrane", "membrane" and the like are used interchangeably herein to describe a material that has a plurality of pores or openings therein. The material is preferably disposable so that in the method of the invention it is used for a single test event and then discarded. It may be comprised of a rigid or flexible substance and is preferably flexible and thin e.g., 5 to 200 microns or more preferably 10 to 50 microns with a tensile strength which can vary significantly and is preferably over 5,000 psi more preferably 10,000 to 50,000 psi. The pores in the membrane are determined based on the size and the number of particles in the test fluid and may be in the range of 0.1 to 100 microns in diameter. The pores in any particular membrane are preferably all substantially the same diameter (±50 to 100%) and shape (either cylindrical or conical). A membrane may include any number of pores but generally includes at least ten pores and preferably includes 10 to 10,000 pores over an area of 1 sq. mm to 1 sq. cm. The porosity of the membrane is the percentage of the area of the membrane which is covered by holes or pores. Thus a 50% porosity means that 50% of the membrane is open due to holes and 50% is membrane. Membranes may have porosities as high as 85%. However, it is difficult to produce membranes of such high porosity while maintaining regularity in pore size and shape. Thus, membrane of the invention generally have a porosity of less that 10%.

The term "carrier" shall mean a liquid, flowable, material which is preferably a pharmaceutically acceptable excipient material which a drug is suspended in or more preferably dissolved in. Preferred carriers include water, ethanol, saline solutions and mixtures thereof with pure water being preferred. Other carriers can be used and include solvents.

The term "measuring" describes an event whereby one or more quantities are measured during the extrusion of a fluid through a porous membrane. The quantity measured may be any quantity which can be directly or indirectly related to the presence of particles in the fluid such as time, pressure, force or a combination of two or more parameters. By relating the measured quantity during extrusion to a precalibrated value it is possible to deduce the size and concentration of particles in the fluid tested.

The term "monitoring" event shall mean measuring a quantity over a period of time e.g., before, after or during extrusion.

The term "placebo" is used herein to describe a carrier without any particles, e.g., pure water.

DISPOSABLE SAMPLE CONTAINER

FIG. 1 is a cross-sectional view of a sample container 1 of the invention which is shaped by a collapsible wall 2. The container 1 has an opening covered by a flexible, porous membrane 3 which is covered by a removable layer 4. The membrane 3 may be rigid and may protrude upward in a convex configuration away from the formulation 5 i.e., the membrane need not be planar as per the membrane of FIG. 4. When the layer 4 is removed the wall 2 can be collapsed thereby forcing the sample fluid 5 (which is preferably a liquid) through the flexible porous membrane 3.

Figure 2:
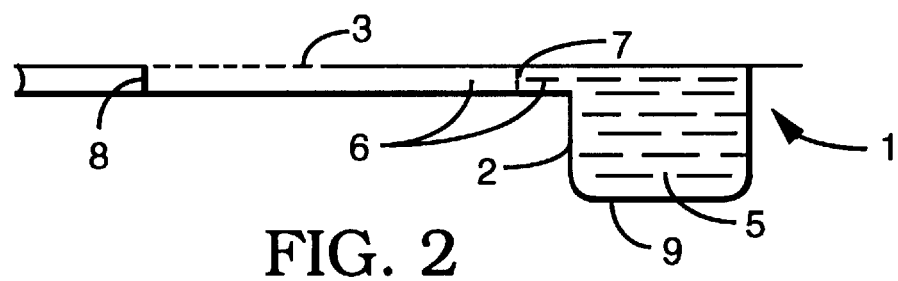
FIG. 2 is a schematic cross-sectional view of another embodiment of a sample container.

FIG. 2 is a cross-sectional view of a more preferred embodiment of a container 1 of the invention. The container is shaped by a collapsible wall 2. The container 1 includes an opening which leads to an open channel 6 which channel 6 includes an abutment 7 which is broken upon the application of force created by sample fluid 5 being forced from the container. When the abutment 7 is broken the sample fluid 5 flows to an area adjacent to the flexible porous membrane 3 and is prevented from flowing further in the channel 6 by a non-breakable abutment 8. The bottom portion 9 of the wall 2 may act as a piston and be slidably movable in the container.

It should be noted that it is possible to carry out the invention without the use of any of the containers of the type shown in FIGS. 1, 2, 4 and 5. The method can be carried out with the use of a porous membrane wherein the porous membrane is placed over an opening of a device and the device is configured so that pressure can be applied to a liquid sample contained in an area adjacent the opening covered by the porous membrane. However, such a configuration has a disadvantage of requiring that the container portion be thoroughly cleaned after each use.

Figure 3:
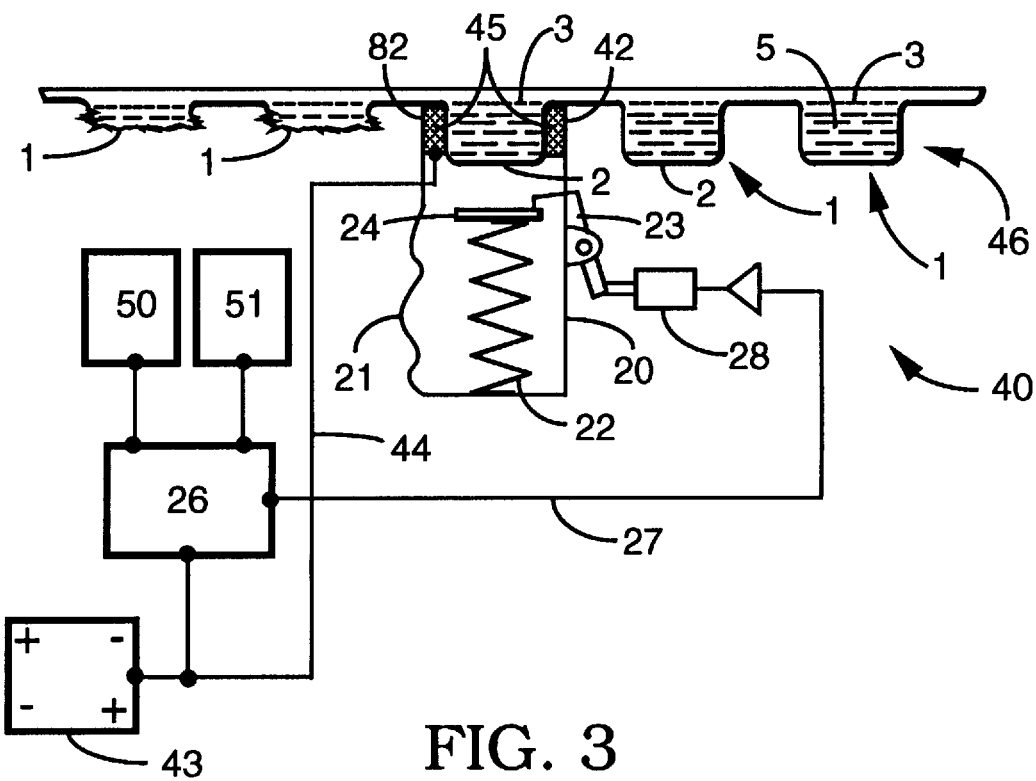
FIG. 3 is a schematic view of a particle detection device of the invention.

FIG. 3 is a cross-sectional view of the container 1 in use. The wall 2 is being crushed by a mechanical component such as the piston 24 shown in FIG. 3. The piston may be driven by a spring 22, or compressed gas. Alternatively, a motor connected to gears can translate the electric motor's circular motion to a cam which crushes the container. The sample fluid 5 is forced into the open channel 6 (breaking the abutment 7 shown in FIG. 2) and against and through the membrane 3. Once the piston 24 has been forced against the sample container wall 2 the container is emptied and used containers are shown to the left in FIG. 3.

The device 40 of FIG. 3 is preferably a hand-held, portable device which is comprised of (a) a device for holding at least one but preferably a number of sample containers, and (b) a means for forcing the contents 5 of a container 1 (on the package) through a porous membrane 3. The device further includes (c) a means for measuring one or more quantities such as the force, time or pressure during extrusion of the fluid 5 through the membrane 3 or measuring a related parameter such as the rate of speed of the extruder over time or the amount of fluid extruded over time. A vibrating means 45 may be positioned sufficiently close to the fluid or membrane such that when activated it aids preventing small particles from accumulating together. The vibrating means is particularly useful when the sample includes a high concentration of very small particles. Such particles may move easily through the pores if separated but accumulate and cause clogging without vibration. The device preferable includes a means for holding and moving one sample container 1 after another into a release position so that a new package is positioned in place for each release and a source of power 43 e.g., conventional batteries.

The device for holding each sample container may be nothing more than a narrow opening created between two outwardly extending bars 42 and 82 or may include additional components for moving new sample containers into position such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move from one container after another into a drug release position. The power source 43 driving the roller(s) is programmed via the microprocessor 26 to rotate the rollers only enough to move from one container 1 to the next. In order to use the device 40, the device 40 must be "loaded," i.e., connected to a sample container having a fluid which is preferably a liquid therein. The entire device 40 is preferably self-contained, light weight (less than 1 kg preferably less than 0.5 kg loaded) and portable. The power source 43 is preferably in the form of standard alkaline batteries. Two 9 volt batteries could supply energy needed to extrude fluid and move one sample container after another into a release position.

Figure 4:
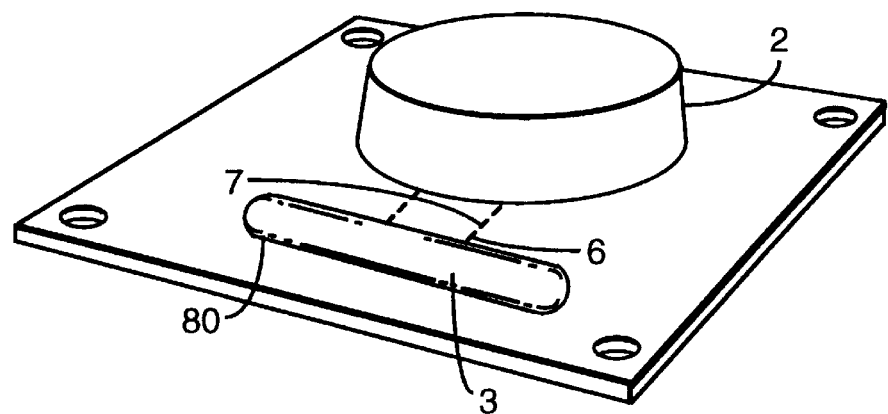
FIG. 4 is a perspective view of the sample container.
Figure 5:
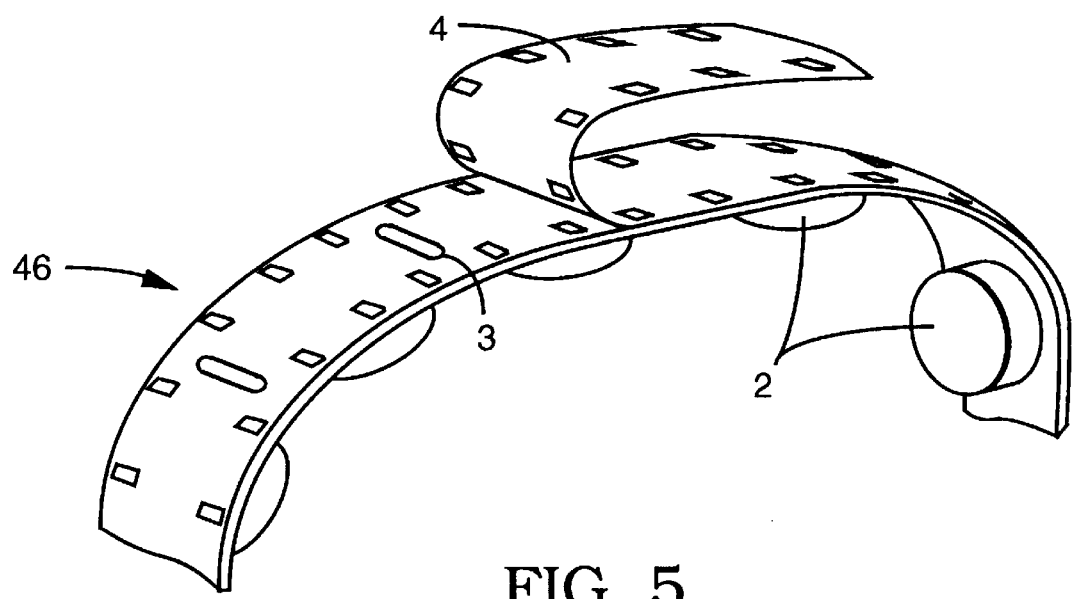
FIG. 5 is a perspective view of a plurality of sample containers linked together.

FIG. 4 is a perspective view of a preferred embodiment of the sample container of the type shown within FIG. 2. However, in the embodiment of FIG. 4 the porous membrane 3 is convexed outward in a raised fashion 80. The container may include a removable cover as per FIG. 1 which could protect the contents from being disturbed during storage or transport. Further, the container could include an opening which would allow the user to place a fluid sample in the container. In some situations it will not be possible to readily determine the size or concentration of the particles within the fluid. In such situations it may be desirable to include sample fluid within a large number of different containers which are linked together as shown within FIG. 5. In FIG. 5 the containers with their collapsible walls 2 are interconnected via an interconnecting means 46 so that the containers can be tested one after another as shown in FIG. 3. In such a configuration the porous membranes 3 will have pores of a different size and/or a different pore density. For example, the pore size could begin as a rather large pore size and move towards a smaller pore size in order to gather data on a quantity such as the amount of pressure, force or time needed to extrude the test fluid through the pore membrane when the pore membrane was being varied with respect to its pore size. The collapsible walls 2 are preferably designed such that when the walls are collapsed against the membrane 3 the entire contents of the container is forced through the porous membrane 3. Thus, it is not desirable for the walls to crumple in an irregular fashion leaving pockets of solution in a partially emptied container 1.

Although the containers can be of any size (e.g., one liter) they are generally constructed so a to include a relatively small amount of sample fluid such as an amount in the range of 10 to 10,000 microliters, more preferably about 100 to 1,000 microliters. Thus, the invention can be carried out with an extremely small amount of sample being tested. Further, once the sample is extruded through the porous membrane 3 the sample can be recovered if desired. Thus, the present invention provides a non-destructive method of analysis.

Because a large number of pores are included in the porous membrane the fluid can be extruded using a relatively low pressure i.e., a pressure in the range of 50 to 600 psi, more preferably 100 to 500 psi. Further, the invention is useful in connection with a wide range of different sample fluids and can include testing gases. More preferably the invention is used to test liquid fluids which have a viscosity in the range of about 25% to 1000% of the viscosity of water.

In some situations it may be desirable to vibrate the porous membrane so as to aid in distributing the particles over the surface of the membrane. For example, vibrations might be applied in an amount in the range of 575 to 32,000, preferably 1,000 to 17,000 and more preferably 2,000 to 4,000 khz. Such vibrations distribute smaller particles which might accumulate and thereby prevent movement through the pores thus allowing for blockage to occur only when the particle size exceeds the size of the pore.

The membrane can have any thickness, but to operate at reduced pressure the membrane generally has a thickness in the range of about 5 to 200 microns or more preferably 10 to 50 microns. The membrane preferably has a tensile strength above about 5,000 psi and may be in the range of 10,000 to 50,000 psi.

In one embodiment of the invention the container includes a bottom wall portion which is slidably positioned within a cylindrical container. Thus, the bottom of the container slides upward in the cylindrical portion and the rate of movement of the bottom piston portion decreases as particles within the test fluid clog the porous membrane. The rate of decrease in the speed of movement is related to a standard or an algorithm in order to determine the concentration and size of particles within the test fluid. More specifically, the greater the rate of decrease in speed in terms of slowing the progress of the bottom portion of the container the greater the concentration and/or size of the particles within the test fluid.

Figure 6:
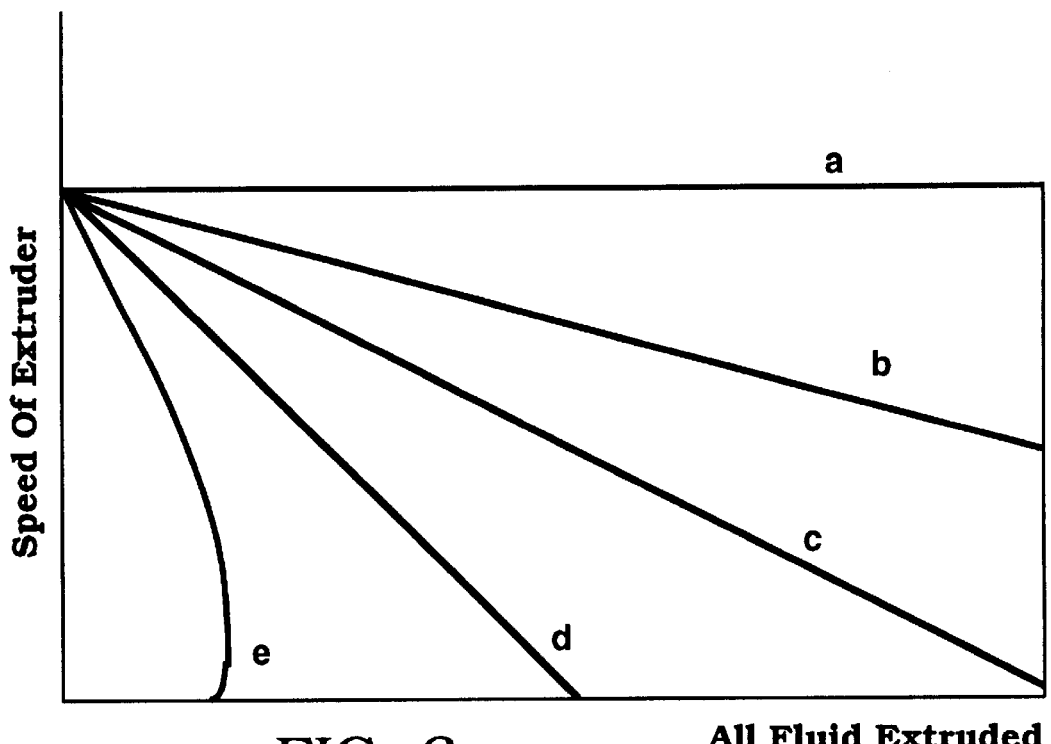
FIG. 6 is a graph showing a theoretical relationship between the speed of an extruder and time.

FIG. 6 is a graph showing a theoretical relationship between time and the speed of an extruder which is either collapsing a collapsible wall 2 of a container 1 or moving a piston or other portion of the container in a manner so as to extrude fluid from the container. As shown in FIG. 6 by line "a" the speed of extrusion remains constant over time if the fluid present within the container does not include particles which are clogged by the pores of the membrane 3. However, when the fluid 5 includes particles in a relatively low concentration the speed of the extruder moving at the contents of the container out of the container begins to decrease over time. The slope of the line "b" becomes steeper over time as more and more particles clog the pores of the membrane. As shown in the line "c" the speed of the extruder can decrease such that it becomes zero at about the point when all material has been extruded from the container. As shown in line "d" the speed of the extruder has become zero prior to a time when all of the contents of the container has been extruded. The line "e" shows a situation where the fluid contains a relatively high concentration of particles which are sufficiently large to clog the pores. Thus, the speed of the extruder decreases on a rather rapid slope over time it becomes zero substantially before all of the fluid 5 within the container 1 has been extruded.

Figure 7:
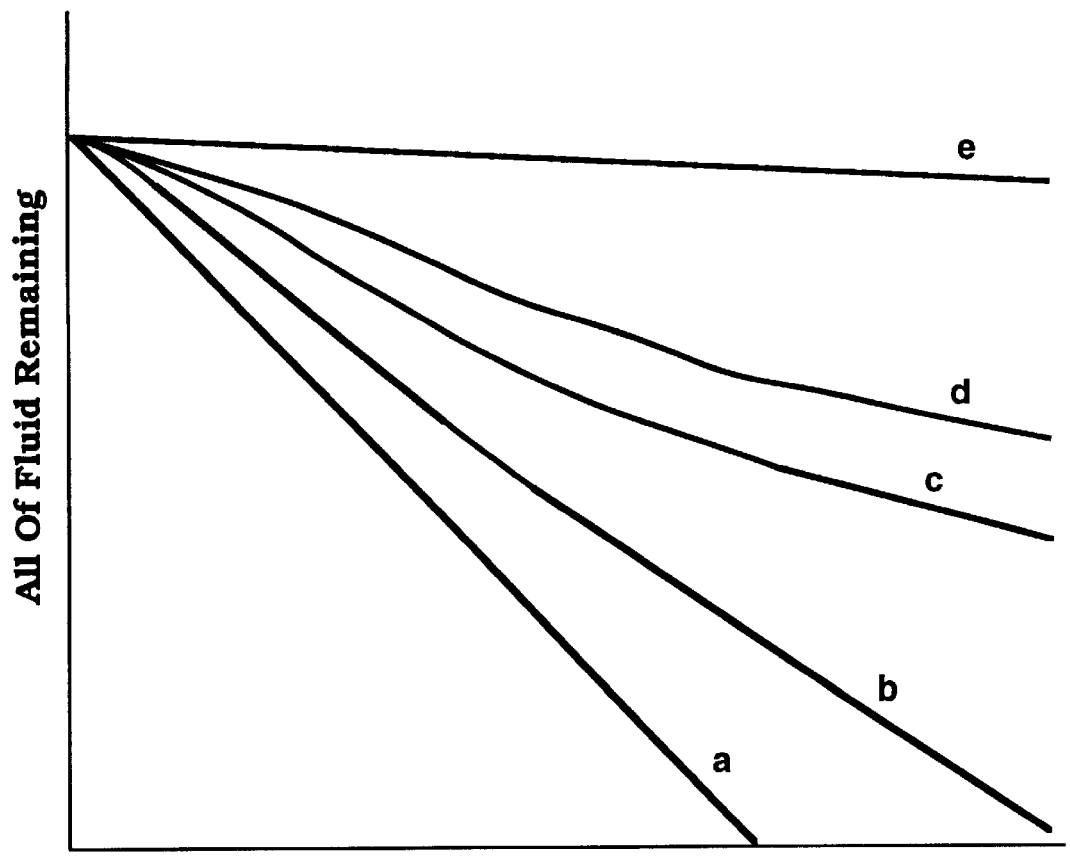
FIG. 7 is a graph showing a theoretical relationship between the amount of fluid remaining and time.

FIG. 7 shows a graph demonstrating a theoretical relationship between the amount of the fluid remaining in the container relative to the time of extrusion. As shown on the line "a" the amount of fluid decreases linearly over time. Such a slope indicates that the fluid does not contain any particles which clog the pores of the membrane. Thus, the rate of extrusion is constant. However, with a sample fluid containing a small concentration of particles sufficiently large to clog the pores the rate of the amount of fluid extruded over time is slower as shown by the line "b". As the concentration and/or size of the number of particles in the fluid increases the rate of decrease of fluid in the container becomes slower over time as shown by line "c" and still slower as shown by line "d". Finally, if the fluid contains a sufficiently high concentration of particles of sufficiently large size clogging will occur relatively quickly and almost none of the fluid will be extruded through the membrane as shown in line "e".

Referring to both FIG. 6 and 7 it can be seen that in certain situations it is desirable to include the sample fluid within additional containers and rerun the test if it is desirable to obtain information indicating something more than the fluid does contain particles. Specifically, in FIG. 6 when the results "d" or "e" are obtained and the speed of the extruder slows to zero before all of the fluid is extruded the test should be rerun with a membrane having a higher pore density or pores of a larger diameter. The same is true with respect to the results shown by the line "e" in FIG. 7. Alternatively, if the results shown by line "a" of FIG. 6 are obtained the test should be rerun with a membrane with smaller diameter holes and/or a lower pore density—the same is true with respect to the results shown by line "a" within FIG. 7.

EXAMPLES

The following Examples are put forth so as to provide those of ordinary skill in the art with a complete disclosure and description of how to carry out the method of the invention and utilize the device of the invention and are not intended to limit the scope of what the inventors regard as their invention. Efforts have been made to insure accuracy with respect to numbers used (amounts, pores diameter and sample volume, etc.) but some experimental errors and deviation should be accounted for. Unless indicated otherwise, parts or parts by weight, molecular weight is weight average molecular weight, temperature is in degrees centigrade at about 20° C., and pressure is at or near atmospheric.

Example 1

Figure 8:
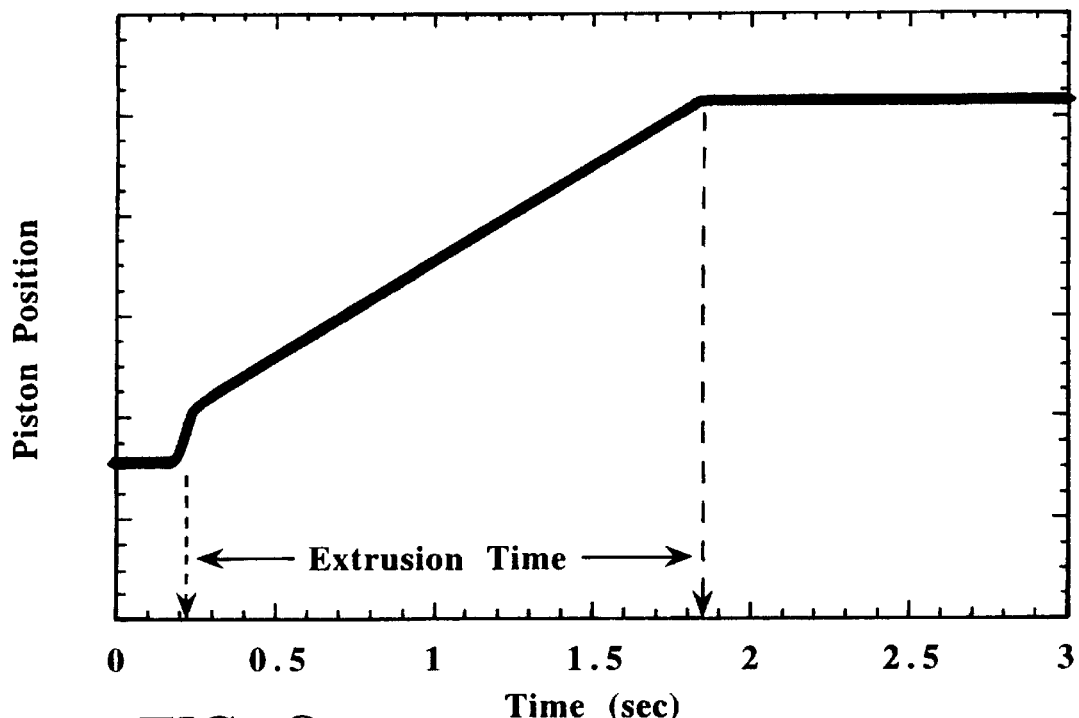
FIG. 8 is an extrusion profile graph for a placebo or particle free sample.
Figure 9:
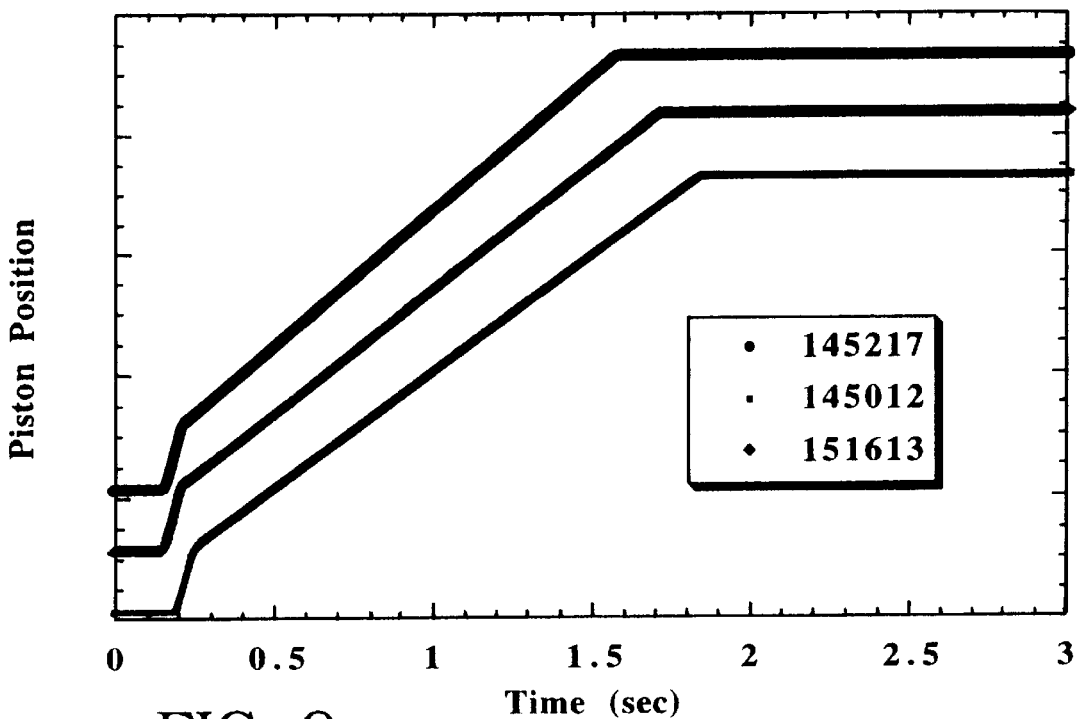
FIG. 9 is a graph showing ana extrusion profile for three particle free solutions.

The sample containers of the type shown in FIG. 2 were prepared wherein the porous membrane included pores having a pore diameter in the range of about 1.8 to 2 microns. In each case the container was filled with a formulation volume of about 45 microliters and the membrane included approximately 215 holes which were positioned in five rows with each row containing approximately 40 to 50 holes. The membrane had a thickness of approximately 0.0096 inches, a length of approximately 0.2 inches and a width of approximately 0.1 inches. The container was filled with pure water and a force of approximately 420 psi was applied. The results are shown in FIG. 8 wherein the position of the piston is measured over time. As can be seen in FIG. 1 the piston moves in a substantially linear manner with the amount of piston movement over time being relatively constant. In FIG. 8 piston movement comes to a halt after slightly more than 1.8 seconds. At this point the container has been completely emptied. The experiment was completed three additional times with pure water and the results are shown in FIG. 9. The extrusion profiles shown in FIGS. 8 and 9 demonstrate that the solution either does not contain any particles or contains particles which are sufficiently small in size relative to the pore size of the membrane so as to not interrupt flow.

Example 2

Figure 10:
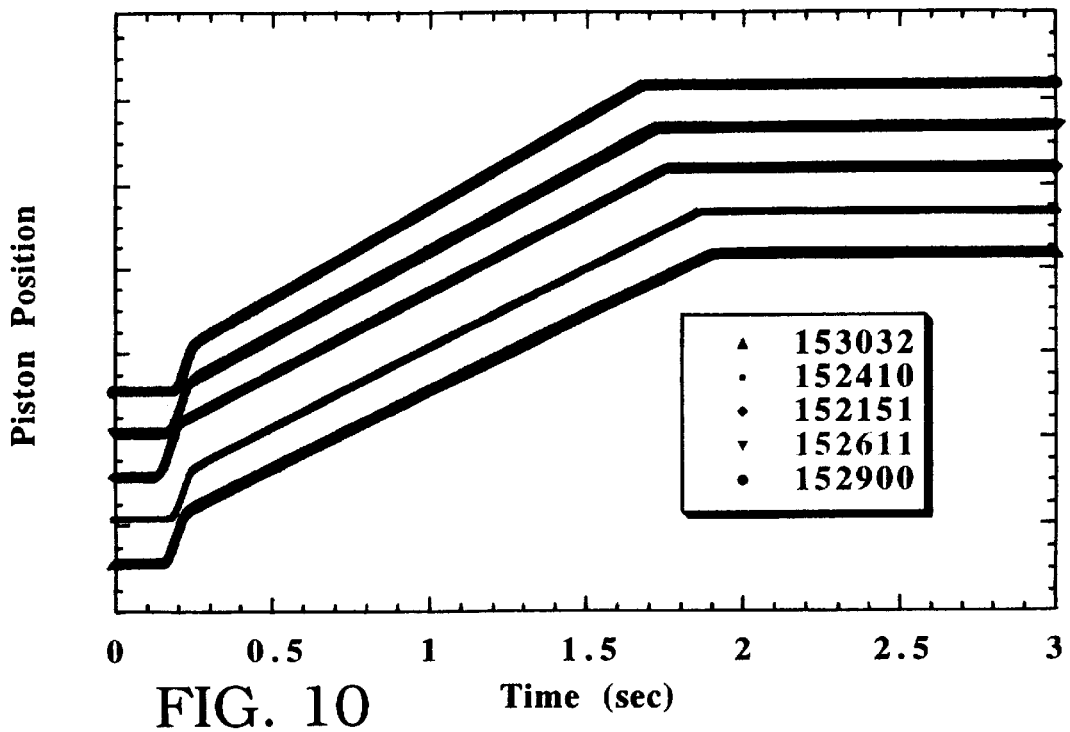
FIG. 10 is a graph showing an extrusion profile for a 0.01% solution of 0.5 micron particles.
Figure 11:
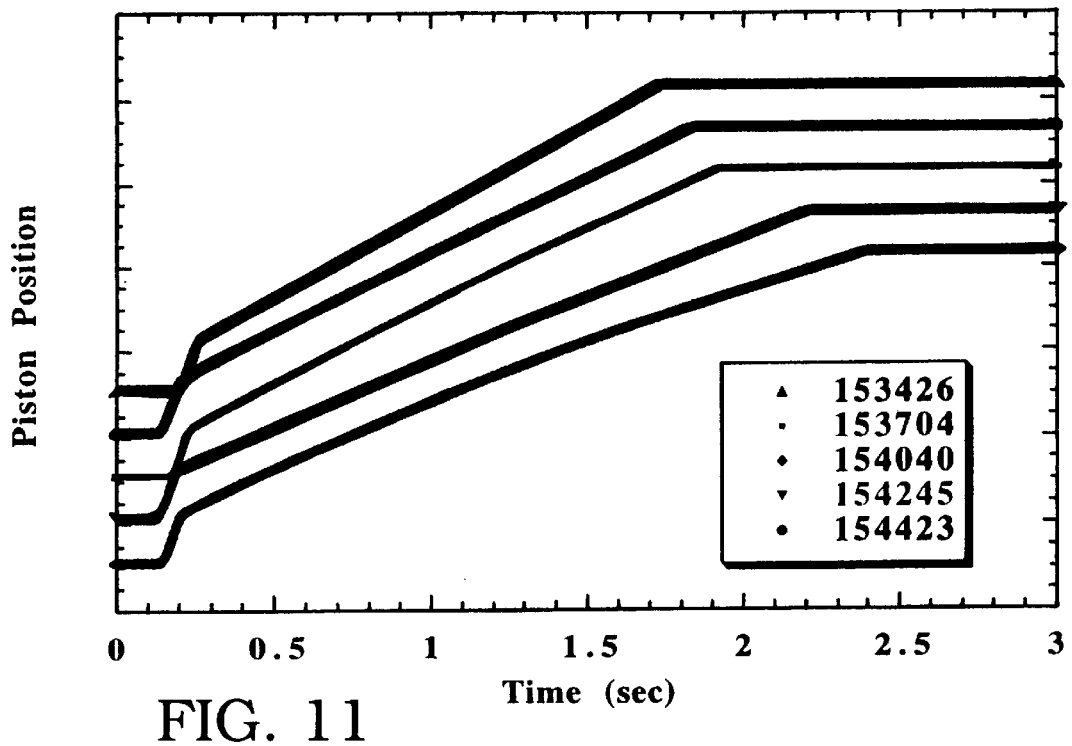
FIG. 11 is an extrusion profile for a 0.1% solution of 0.5 micron particles.

Containers of the type described in Example 1 were prepared. The containers were filled to a volume of 45 microliters with water containing different concentrations of polystyrene beads having a diameter of about 0.5 micron. In a first set of experiments five separate containers containing 0.01% of polystyrene beads of a diameter of 0.5 micron were extruded by the application of force of approximately 420 psi. The results obtained are shown in FIG. 10. Due to the small size of the beads relative to the size of the pores the extrusion profile remains substantially linear. Similar results were obtained when the concentration of the beads was increased to 0.1% beads in pure water. Using such a sample five separate extrusions were tested and the results are shown in FIG. 11. The percentage amount of beads was increased to 1.0% and five additional extrusions were made with five different containers. The results obtained are shown in FIG. 12.

Example 3

Figure 14:
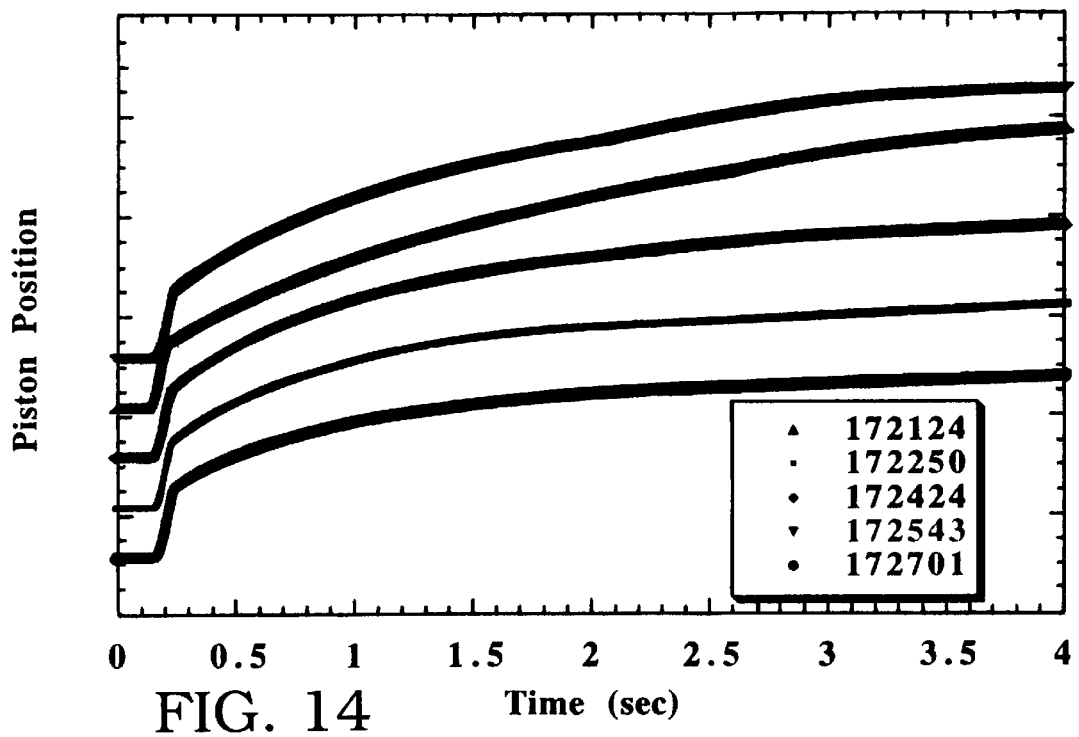
FIG. 14 is an extrusion profile for a 0.1% solution of 1.0 micron particles.
Figure 15:
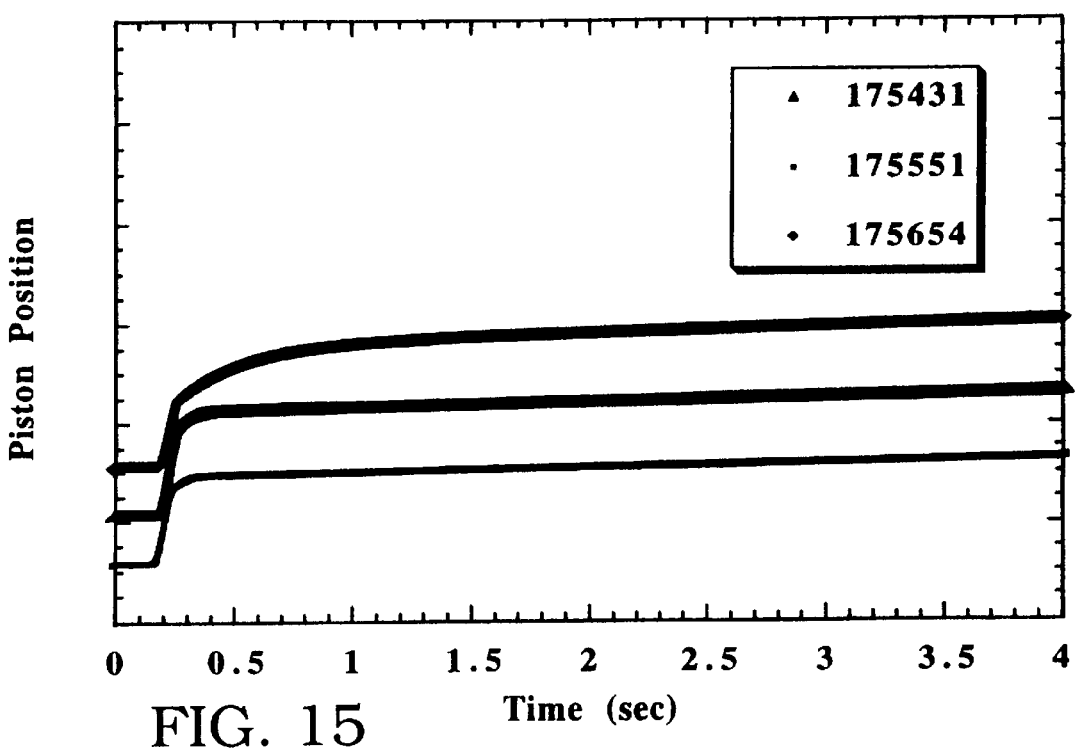
FIG. 15 is an extrusion profile for a 1.0% solution of 1.0 micron particles.

Additional containers were prepared as per Examples 1 and 2. The containers were filled with 45 microliters of differing concentrations of polystyrene beads as per Example 2. Specifically, the concentration of the beads was 0.01%, 0.1% and 1%. However, for Example 3 the size of the beads was increased to 1.0 micron. The extrusion profile for the concentration at. 0.01% is shown in FIG. 13. The extrusion profile at 0.1% is shown in FIG. 14 and the extrusion profile using a sample with beads present in an amount of 1.0% is shown in FIG. 15. Even though the size of the beads is smaller than the pore size the beads clogged the hole significantly at 0.1% shown in FIG. 14 and have a significant effect on clogging the holes as shown in FIG. 15 when present in a concentration of about 1%.

Example 4

Figure 16:
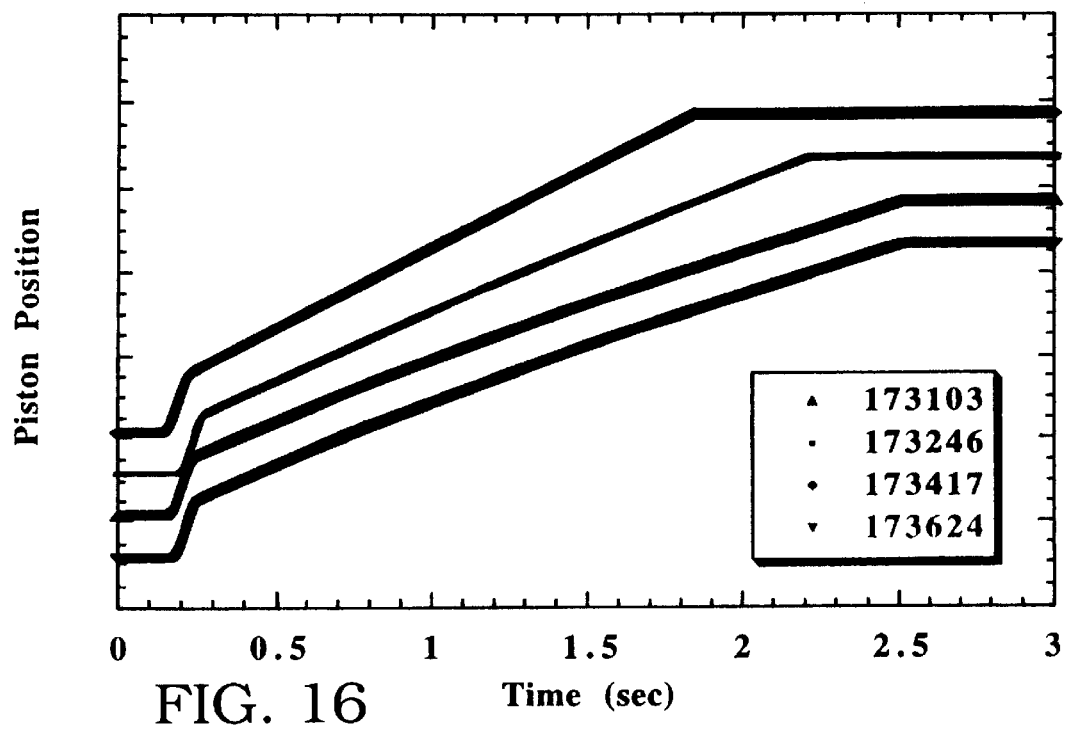
FIG. 16 is an extrusion profile for a sample containing approximately 53,000 2.0 micron particles.
Figure 18:
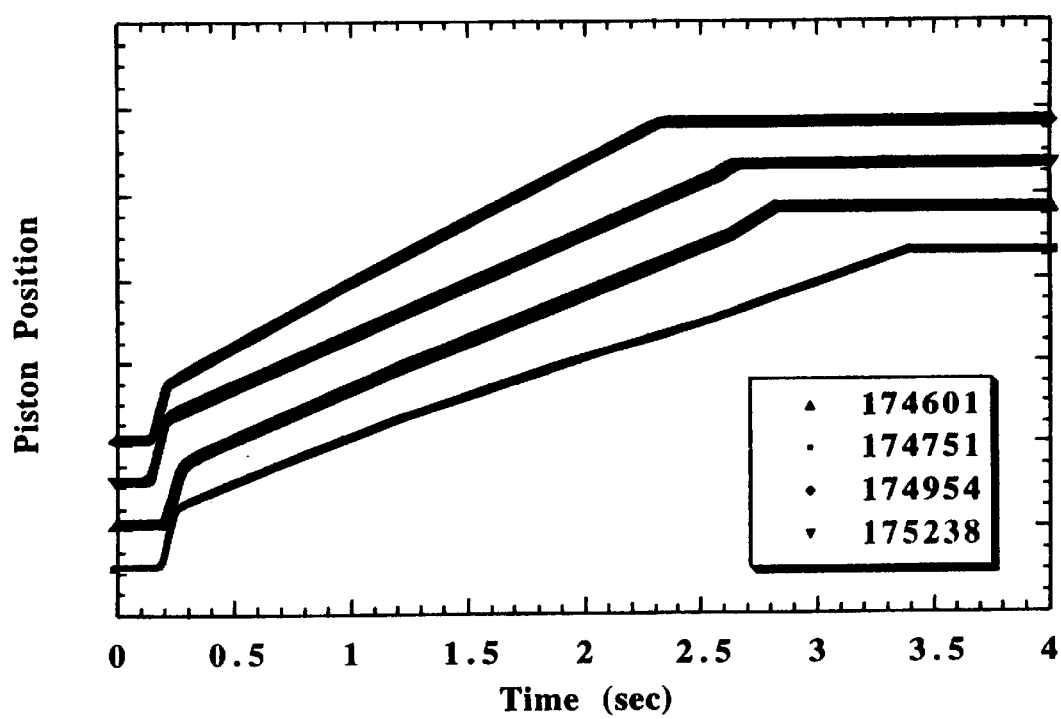
FIG. 18 is an extrusion profile for a sample containing approximately 530 2.0 micron particles.

Containers of the type described in Example 1 were prepared. Sample formulations placed in the containers were prepared as per Examples 2 and 3. However, the size of the polystyrene beads was increased to approximately 2.0 microns. In a first group of containers 2.0 micron beads were added in an amount of approximately 530 beads for FIG. 16, approximately 5,300 beads for FIG. 17 and approximately 53,000 beads for the profile shown in FIG. 18.

CALIBRATION

Results such as those shown in FIGS. 8–18 can be used to calibrate a standard against which an unknown sample can be compared. Further, combinations of different size beads at varying concentrations can also be prepared to develop different extrusion profiles to be used for calibration purposes. In the examples wherein profiles shown in FIGS. 8–18 were generated the containers included water with polystyrene beads. However, the water can be substituted for other carriers and the polystyrene beads substituted with other particle components of varying sizes and shapes. When carrying out tests it is preferable to compare any actual samples tested with calibrated results obtained using the same carrier liquid and the same approximate size, shape and concentration of particles.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

What is claimed is:

1. A device for measuring a size or number of particles in a sample fluid, comprising:

a container for holding the sample fluid to be tested, the container having an opening therein and a wall collapsible by an application of force;

a porous membrane having a plurality of pores therein, wherein the pores have a diameter in a range of 0.1 to 100 microns a fluid connection between the container opening and the porous membrane;

a means for forcing the sample of fluid through the porous membrane by applying force to the collapsible wall of the container;

a measurement component which measures a quantity selected from a group consisting of: (a) time needed to extrude the sample of fluid through the porous membrane wherein the time is measured by a timing means; (b) pressure needed to extrude the sample of fluid through the porous membrane wherein the pressure is measured by a pressure detection means; and (c) force needed to extrude the sample of fluid through the porous membrane wherein force is measured by a force measurement means; and a detection means for relating the measured quantity to the size and number of particles in the sample fluid.

2. The device of claim 1, wherein the porous membrane includes at least ten pores.

3. The device of claim 1, wherein the pores are present in a pore density of 10 to 10,000 pores per 1 sq. mm to 1 sq. cm.

4. The device of claim 1, wherein said detection means comprises:

a microprocessor having a look-up table or an algorithm stored in a memory, for relating the measured quantity to the size or number of particles in the sample.

* * * * *